United States Patent
Shapiro et al.

(12)

(10) Patent No.: US 6,432,424 B1
(45) Date of Patent: Aug. 13, 2002

(54) COSMETIC COMPOSITIONS CONTAINING CREATINE, CARNITINE, AND/OR PYRUVIC ACID

(75) Inventors: Stanley S. Shapiro, Livingston; Katharine M. Martin, Ringoes; Steven A. Shaya, Highlands; Claudia K. Kaminski, Milford, all of NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/606,491

(22) Filed: Jun. 29, 2000

(51) Int. Cl.$^7$ ................................................. A61K 6/00
(52) U.S. Cl. ....................... 424/401; 514/458; 514/474; 514/557; 514/561; 514/725; 514/846; 514/847; 514/938; 514/944
(58) Field of Search .......................... 401/424; 514/784, 514/873, 886, 506, 458, 474, 557, 561, 725, 846, 847, 938, 944; 424/401

(56) References Cited

U.S. PATENT DOCUMENTS

| | | |
|---|---|---|
| 3,755,560 A | 8/1973 | Dickert et al. |
| 4,254,105 A | 3/1981 | Fukuda |
| 4,320,145 A | 3/1982 | Cavazza |
| 4,421,769 A | 12/1983 | Dixon et al. |
| 4,960,764 A | 10/1990 | Figueroa, Jr. et al. |
| 4,961,927 A | 10/1990 | Kogure |
| 5,106,624 A | 4/1992 | Bertini |
| 5,376,379 A | 12/1994 | Fabre et al. |
| 5,531,993 A | 7/1996 | Griat |
| 5,536,751 A | 7/1996 | Bunger |
| 5,578,312 A | 11/1996 | Parrinello |
| 5,627,212 A | 5/1997 | Cavazza et al. |
| 5,637,305 A | 6/1997 | Cavazza et al. |
| 5,641,814 A | 6/1997 | Martin |
| 5,690,946 A | 11/1997 | Koulbanis et al. |
| 5,756,107 A | 5/1998 | Hahn et al. |
| 5,759,610 A | 6/1998 | Nishimoto et al. |
| 5,821,237 A * | 10/1998 | Bissett et al. ................. 514/75 |
| 5,928,657 A | 7/1999 | Simon |
| 5,932,234 A | 8/1999 | Simon et al. |
| 5,935,636 A | 8/1999 | Nishimoto et al. |
| 5,951,990 A * | 9/1999 | Ptchelintsev ................ 424/401 |
| 5,997,885 A | 12/1999 | Koulbanis et al. |
| 6,033,684 A | 3/2000 | Norcia |
| 6,106,846 A | 8/2000 | Breton et al. |

FOREIGN PATENT DOCUMENTS

| | | |
|---|---|---|
| EP | 0 413 528 A1 | 2/1991 |
| EP | 0 559 502 A1 * | 1/1993 |
| EP | 0 573 465 B1 | 12/1993 |
| EP | 0 600 730 B1 | 6/1994 |
| EP | 0273202 B1 | 6/1995 |
| EP | 0 711 543 A1 | 5/1996 |
| EP | 0 717 984 A2 | 6/1996 |
| EP | 0 868 916 A2 | 10/1998 |
| EP | 0 974 342 A1 | 1/2000 |
| EP | 0 983 727 A2 | 3/2000 |
| EP | 0 998 914 A1 | 5/2000 |
| FR | 1248192 | 10/1960 |
| FR | 3574 M | 9/1965 |
| FR | 2619007 A | 2/1989 |
| FR | 2627385 A | 8/1989 |
| GB | 0559502 | 3/1996 |
| GB | 0699432 | 1/1997 |
| GB | 0773012 | 11/1997 |
| GB | 0846462 | 12/1999 |
| WO | 84/04885 A1 | 12/1984 |
| WO | 89/06958 A1 | 8/1989 |
| WO | 95/03028 A1 | 2/1995 |
| WO | 95/04537 A1 | 2/1995 |
| WO | 95/13793 A1 | 5/1995 |
| WO | 95/27501 A1 | 10/1995 |
| WO | 96/11572 A1 | 4/1996 |
| WO | 97/15282 A1 | 5/1997 |
| WO | 98/51277 A1 | 11/1998 |
| WO | 99/07388 A1 | 2/1999 |
| WO | 99/08681 A1 | 2/1999 |
| WO | 00/04870 A2 | 2/2000 |

OTHER PUBLICATIONS

Balsom, P., Soderlund, K. and Ekbom, B., Creatine in Humans with Special Reference t Creatine Supplementation, Sports Med. 1994, 268–280, 18 (4).

Bremer, J., Carnitine–Metabolism and Functions, Physiological Reviews, 1983, 1420–1480, vol. 63 No. 4.

Stanko, R., Tietze, D and Arch, Body Compositin, energy utilization, and nitrogen metabolism with a 4.25–MJ/d low–energy diet supplemented with pyruvate, American Journal Clinical Nutr. 1992, 630–635, vol. 56 (4).

Evian "Le brumisateur©", S.A. des Eaux Minerales d'Evian, excerpt taken from Water . . . It's Life., Evian publication dated May 1997.

Medical Guide to the Mineral Waters of France and its Wintering Stations, A. Vintras, M.D., 1883, J&A Churchill, London, pp. 261–263.

Balsam, M. S. and Sagarin, E.., Cosmetics Science And Technology, vol. 1, Second Ed. John Wiley & Sons, Inc. (1972), pp. 72–73 and 443–465.

McCutcheon's Emulsifiers & Detergents, pp. 317–324 (1986), MC Publishing, New Jersey.

Wenniger, J. A. et al. International Cosmetic Ingredient Dictionary and Handbook, vol. 2, $7^{th}$ Ed. (1997), pp. 1612, 1613, 1626, 1654–1661, 1673–1686, 1693–1697.

Abstract of JP 51148042 publication date Dec. 17, 1976 on Database WEST, DWPI.

* cited by examiner

*Primary Examiner*—Minna Moezie
*Assistant Examiner*—Alysia Berman
(74) *Attorney, Agent, or Firm*—William E. McGowen

(57) ABSTRACT

The present invention relates to a cosmetic composition comprising (i) a compound selected from the group consisting of creatine, carnitine, and pyruvic acid, and a cosmetically acceptable salt or ester thereof, (ii) a nutrient, and (iii) a skin-conditioning agent selected from the group consisting of an emollient and a humectant.

24 Claims, No Drawings

COSMETIC COMPOSITIONS CONTAINING CREATINE, CARNITINE, AND/OR PYRUVIC ACID

FIELD OF THE INVENTION

The present invention relates to a cosmetic composition comprising (i) a compound selected from the group consisting of creatine, carnitine, and pyruvic acid, and a cosmetically acceptable salt or ester thereof, (ii) a nutrient, and (iii) a skin-conditioning agent.

BACKGROUND OF THE INVENTION

Carnitine is an amino acid that is synthesized endogenously in the liver from its amino acid precursors lysine and methionine. This water soluble amino acid is found in highest concentrations in the adrenal glands, skeletal, and cardiac muscle, and smaller concentrations are found in the kidneys and brain. This distribution of carnitine in the body reflects the utilization of fatty acids by the tissues as a source of energy. Carnitine functions as a biocatalyst to carry long and medium length chain fatty acids across the cell wall and into the mitochondria where fats are metabolized for energy production. The absence of proper levels of carnitine in the cells may result in poor metabolism of fatty acids which can cause buildup within the cell and its surroundings to eventually lead to elevated blood fat and triglyceride levels. During the last decade, carnitine has seen increase use for muscle efficiency since fatty acid oxidation within the mitochondria is the muscle's major source of energy. Carnitine is also used to improve fat metabolism and to reduce blood triglycerides. See, e.g., Bremer, J. "Carnitine, Metabolism and Functions" Physiology Review. 63:1420–1480 (1983); Opie, L. H. "Role of Carnitine in Fatty Acid Metabolism of Normal and Ischemic Myocardium", Am. Heart Journal, 3:375–377 (1974); and Stryer, L. "Biochemistry", $3^{rd}$ ed., (1988, W.H. Freeman and Company, New York).

Creatine is synthesized in the liver and is supplemented by a diet of meat and fish. Ninety-five percent of the body's creatine supply is found in the skeletal muscles. Creatine, which is converted into creatine phosphate within cells, increases the availability of energy to the cell in the form of adenosine triphosphate (ATP). Cells rely on energy produced in the Krebs cycle from the dephosphorylation of ATP to adenosine diphosphate (ADP). Creatine phosphate can then donate a phosphate group to ADP, recreating ATP and, thus, extending the energy generating biochemical pathways within cells. See, e.g. Balsom, P. D., et al. "Creatine in humans with special reference to creatine supplementation", Sports-Med., 18(4):268–280 (1994) and Stryer, L. "Biochemistry", $3^{rd}$ ed., 1988, W.H. Freeman and Company, New York.

Pyruvate, the key glycolytic intermediate of all mammalian cells, is created during the metabolism of carbohydrates and protein. In addition to being formed in the body, pyruvate is present in foods including red apples, cheese, and red wine. The oxidation of pyruvate in the Krebs cycle provides cells with the bulk of adenosine triphosphate (ATP) used to maintain homeostasis. In cells with high energy charge, coenzyme A (CoA) is acylated as acetyl-CoA which activates pyruvate carboxylase, directing pyruvate toward gluconeogenesis. However, when energy is low in the cell, CoA is not acylated and pyruvate is preferentially oxidized via pyruvate dehydrogenase to $CO_2$ and $H_2O$. Through its role as an energy source, pyruvate has been suggested to aid weight loss efforts and exercise endurance. See, e.g., Stanko, R. T., Tietze, D. L., and Arch, J. E. "Body composition, energy utilization, and nitrogen metabolism with a 4.25-MJ/d low-energy diet supplemented with pyruvate," Am J Clin Nutr, 56(4), 630–635 (1992) and Stryer, L. "Biochemistry", $3^{rd}$ ed. (1988, W.H. Freeman and Company, New York).

SUMMARY OF THE INVENTION

The present invention relates to a cosmetic composition comprising (i) a compound selected from the group consisting of creatine, carnitine, and pyruvic acid, and a cosmetically acceptable salt or ester thereof, (ii) a nutrient, and (iii) a skin-conditioning agent selected from the group consisting of an emollient and a humectant.

In one embodiment, the invention features a topical cosmetic composition comprising (i) a compound selected from the group consisting of creatine, carnitine, and pyruvic acid, and a cosmetically acceptable salt or ester thereof, (ii) a nutrient, (iii) a skin-conditioning agent selected from the group consisting of an emollient and a humectant, and (iv) a cosmetically-acceptable topical carrier.

In one embodiment, the invention also features methods of topically administering such compositions. The compositions of the present invention can enhance the uptake of oxygen, water, and nutrients into the skin (e.g., skin cells), enhance skin cell metabolism, reduce the loss of skin firmness and elasticity, and/or have a reduced incidence of eye irritation.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to cosmetic composition. In one embodiment, the composition comprises mineral water. What is meant by mineral water is water having mineralization (i.e., the sum of the concentrations of anions and cations present in the water) of at least about 200 mg/L (e.g., at least about 300 mg/L such from about 400 mg/L to 1000 mg/L). In one embodiment, the mineral water comprises at least about 10 mg/L, e.g., at least about 20 mg/L, of calcium and at least about 5 mg/L, e.g., at least about 10 mg/L, of magnesium. Examples of such anions and cations include, but are not limited to, calcium, magnesium, bicarbonates, sulfates, potassium, sodium, chlorides, nitrates, phosphates, lithium, manganese, sulfites, fluoride, and iodide.

The mineral water may be a naturally mineralized water, e.g., a mineral water suitable for consumption, or a thermal spring water, which is often not consumable. Examples of mineral water include, but are not limited to, eau d'Evian (Evian Eau Minerale Naturelle or Evian® Natural Spring Water and referred herein as Evian® Mineral Water), eau Volvic, and eaux de Vittel (e.g., Grande Spring or Hepar Spring). Examples of thermal spring waters include eau de la Bourboule, eau d'Enghien-les-bains, eau d'Allevard-les-bains, eau de Digne, eau des Maizieres, eau de Nyrac-les-bains, eau de Lons le Saunier, Eaux Bonnes, eau de Rochefort, eau de Saint Christau, eau des Fumades, eau de Tereau de Vittel, eaux du bassin de Vichy, eau d'Uriage, eau d'Avene, and eau de la Roche Posay.

In one embodiment, the mineral water comprises (a) from about 30 mg/L to about 150 mg/L of calcium; (b) from about 10 mg/L to about 50 mg/L of magnesium; (c) from about 150 mg/L to about 700 mg/L of bicarbonates; (d) from about 0.1 mg/L to about 5 mg/L of potassium; (e) from about 1 to about 20 mg/L of sulfates; (f) from about 1 to about 10 mg/L of sodium; (g) from about 1 mg/L to about 10 mg/L of chlorides; and (h) from about 1 mg/L to about 10 mg/L of nitrates.

In one embodiment, the mineral water is Evian® Mineral Water that comprises: (a) about 78 mg/L of calcium; (b) about 24 mg/L of magnesium; (c) about 357 mg/L of bicarbonates; (d) about 1 mg/L of potassium; (e) about 10 mg/L of sulfates; (f) about 5 mg/L of sodium; (9) about 4 mg/L of chlorides; and (h) from about 1 to about 4 mg/L nitrates.

The compositions of the present invention comprise one or more of the following compounds: creatine, carnitine, or pyruvic acid, or a cosmetically acceptable salt or ester thereof. What is meant by cosmetically acceptable salt or ester is one that does not eliminate the therapeutic benefit of the compound (e.g., its hydrating, nourishing, or metabolic enhancing properties). Examples of cosmetically acceptable salts, include, but are not limited to, those with cosmetically acceptable organic acids (e.g., acetic, lactic, maleic, citric, malic, ascorbic, succinic, benzoic, methesulfonic, toluenesulfonic, or pamoic acid), as well as polymeric acids (e.g., tannic or carboxymethyl cellulose) and salts with inorganic acids such as a hydrohalic acid (e.g., hydrochloric acid, sulfuric acid, or phosphoric acid). Examples of cosmetically acceptable esters include, but are not limited to, $C_2$–$C_6$ alkyl esters such as methyl esters and ethyl esters. Examples of such compounds include, but are not limited to, creatine monohydrate, creatine hemisulfate, D-carnitine, L-carnitine, L-carnitine hydrochloride, sodium pyruvate, and pyruvic acid methyl ester. As used herein, if the stereochemistry of the compound is not indicated, then the compound includes all stereoisomers, if any.

What is meant by a nutrient is an organic substance occurring in foods that is not synthesized by the body and is necessary in trace amounts for the normal metabolic functioning of the body, such as vitamins, essential amino acids, and essential fatty acids.

Examples of such vitamins include, but are not limited to, vitamin A, a vitamin B (e.g., vitamin B1, vitamin B2, vitamin B6, or vitamin B12), vitamin C, and a vitamin E (e.g., a tocopherol or a tocotrienol), and a cosmetically acceptable salts or esters thereof, such a retinyl palmitate, retinyl acetate, tocopherol succinate, and tocopherol acetate.

Examples of such essential amino acids include, but are not limited to, arginine, histidine, isoleucine, leucine, lysine, methionine, phenylalanine, threonine, tryptophan, and valine.

Examples of essential fatty acids include, but are not limited to, linoleate and linolenate.

What is meant by an emollient is a compound that helps to maintain the soft, smooth, and pliable appearance of the skin (e.g., by remaining on the skin surface or in the stratum corneum to act as a lubricant). Examples of emollients can be found on pages 1657–1661 of the International Cosmetic Ingredient Dictionary and Handbook, eds. Wenninger and McEwen, pp. 1612–13, 1626, and 1654–55 (The Cosmetic, Toiletry, and Fragrance Assoc., Washington, D.C., 7$^{th}$ Edition, 1997) (hereinafter "ICI Handbook"), and include, but are not limited to, hexyldecyl stearate and plant, nut, and vegetable oils such as macadamia nut oil, rice bran oil, grape seed oil, palm oil, primrose oil, hydrogenated peanut oil, olive oil, and avocado oil.

What is meant by a humectant is a compound intended to increase the water content of the top layers of skin (e.g., hygroscopic compounds). Examples of humectants can be found on pages 1661–1662 of the ICI Handbook and include, but are not limited to, glycerin or trehalose (e.g., $\alpha,\alpha$-trehalose, $\beta,\beta$-trehalose, $\alpha,\beta$-trehalose) or a salt or ester thereof (e.g., trehalose 6-phosphate).

The amount of carnitine or a cosmetically acceptable salt or ester thereof, creatine or a cosmetically acceptable salt or ester thereof, pyruvic acid or a cosmetically acceptable salt or ester thereof, nutrient, emollient, or humectant in the composition varies (e.g., depending on the intended use and the form of the composition) will typically be present in the composition in an amount from about 0.001% to about 20%, by weight, of the topically applied composition, e.g., from about 0.01% to about 10%, by weight, such as from about 0.01% to about 5%, by weight, of such emollient or humectant and from about 0.001% to about 10%, by weight, of the topically applied composition, e.g., from about 0.01% to about 5%, by weight, such as from about 0.01% to about 1%, by weight, of such carnitine, creatine, pyruvic acid or cosmetically acceptable salt or ester thereof.

In one embodiment, the composition further comprises another cosmetically active agent. What is meant by a "cosmetically active agent" is a compound that has a cosmetic or therapeutic effect on the skin, e.g., agents to treat wrinkles, acne, or to lighten the skin. In one embodiment, the agent is selected from, but not limited to, the group consisting of hydroxy acids, benzoyl peroxide, sulfur resorcinol, ascorbic acid, D-panthenol, hydroquinone, sunscreen agents, anti-inflammatory agents, skin lightening agents, antimicrobial and antifungal agents, estrogens, 2-dimethylaminoethanol, lipoic acid, amino acids such a proline and tyrosine, lactobionic acid, acetyl-coenzyme A, niacin, riboflavin, thiamin, ribose, electron transporters such as NADH and FADH2, botanical extracts such as aloe vera and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of hydroxy acids include, but are not limited, to (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

The compositions of the present invention can be used by topically administering it to a mammal, e.g., by the direct laying on or spreading of a cosmetic containing the mineral water on the skin of a human. The cosmetic compositions useful in the subject invention involve formulations suitable for topical application to mammalian skin, the formulation comprising (i) mineral water, (ii) optionally, a safe and effective amount of the creatine, carnitine, or pyruvic acid, or a cosmetically acceptable salt or ester thereof, (iii) optionally a nutrient, an emollient, humectant (e.g., trehalose), or other cosmetically active agent(s), and (iv) optionally, a cosmetically-acceptable topical carrier. The term "cosmetically-acceptable topical carrier" refers to a carrier for topical use that is capable of having the mineral water and any other agents dispersed or dissolved therein, and possessing acceptable safety properties.

The topical compositions useful in the present invention may be used for a variety of cosmetic uses, including, but not limited to, treating, cleansing, beautifying, or covering the skin or hair of a human. The compositions, thus, may be made into a wide variety of product types. These include, but are not limited to lotions, creams, gels, sticks, sprays, ointments, pastes, mousses, shampoos, cosmetics, and dermal patches. Products include but are not limited to, lip balms, moisturizing and sunscreen lotions/creams, skin cleansing compositions (e.g., facial scrubs), and body mists. These products may comprise several types of carrier systems including, but not limited to single phase solutions (e.g., water, such as mineral water, or oil based solutions), emulsions, and gels.

The topical compositions useful in the present invention formulated as solutions typically include a cosmetically acceptable aqueous (e.g. mineral waters and/or organic carriers, e.g., from about 80% to about 99.99, by weight of the composition, such as from about 90% to about 99%, by weight of the composition, of an acceptable aqueous or organic solvent). Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, butanediol, and mixtures thereof.

If the topical solution useful in the present invention are formulated as an aerosol and applied to the skin as a spray-on, a propellant is added to a solution composition. Examples of propellants useful herein include, but are not limited to, chlorinated, fluorinated, and chloro-fluorinated lower molecular weight hydrocarbons. Other propellants useful herein can be found in Sagafin, Cosmetics Science and Technology, 2nd Edition, Vol. 2, pp. 443–65 (1972) (hereinafter "Sagafin") and the ICI Handbook pp. 1655.

A lotion can be made from a solution carrier system. Lotions typically comprise from about 1% to about 20% by weight of the composition (e.g., from about 5% to about 10%) of an emollient(s) and from about 50% to about 90% by weight of the composition (e.g., from about 60% to about 80%) of water.

Another type of product that may be formulated from a solution carrier system is a cream. A cream typically comprises from about 5% to about 50% by weight of the composition (e.g., from about 10% to about 20%) of an emollient(s) and from about 45% to about 85% by weight of the composition (e.g., from about 50% to about 75%) of water (e.g., mineral water).

Yet another type of product that may be formulated from a solution carrier system is an ointment. An ointment may comprise a simple base of animal or vegetable oils or semi-solid hydrocarbons. Ointments may also comprise absorption ointment bases that absorb water to form emulsions. Ointment carriers may also be water-soluble. An ointment may comprise from about 1% to about 20% by weight of the composition of an emollient(s) plus from about 0.1% to about 2% by weight of the composition of a thickening agent(s). A more complete disclosure of thickening agents or viscosity increasing agents useful herein can be found in Sagafin pp. 72–73 and the ICI Handbook pp. 1693–97.

If the carrier is formulated as an emulsion (e.g., an oil-in-water, silicone-in-water, water-in-oil, or water-in-silicone emulsion), from about 1% to about 10% by weight of the composition (e.g., from about 2% to about 5%) of the carrier system may comprise an emulsifier(s). Emulsifiers may be nonionic, anionic, cationic, or zwitterionic. Suitable emulsifiers are disclosed in, for example, U.S. Pat. No. 3,755,560, U.S. Pat. No. 4,421,769, McCutcheon's Detergents and Emulsifiers, North American Edition, pp. 317–24 (1986), and the ICI Handbook, pp.1673–86.

Lotions and creams can also be formulated as emulsions. Typically, such emulsions may comprise from 0.5% to about 5% by weight of the composition of an emulsifier(s). Creams may typically comprise from about 1% to about 20% by weight of the composition (e.g., from about 5% to about 10%) of an emollient(s); from about 20% to about 80% by weight of the composition (e.g., from about 30% to about 70%) of water (e.g. mineral water); and from about 1% to about 10% by weight of the composition (e.g., from about 2% to about 5%) of an emulsifier(s).

Two phase emulsion skin care preparations, such as lotions and creams, of the oil-in-water type and water-in-oil type are well-known in the cosmetic art and are useful in the subject invention. Triphase emulsion compositions, such as the water-in-oil-in-water type, as disclosed in U.S. Pat. No. 4,254,105, are also useful in the subject invention. In general, such triphase emulsions contain water, emollients, and emulsifiers as essential ingredients. Triple emulsion carrier systems comprising an oil-in-water-in-silicone fluid emulsion composition, as disclosed in U.S. Pat. No. 4,960,764, may also be useful in the subject invention.

The compositions of the present invention may also comprise one or more of the following: antioxidants (e.g., ascorbic acid, tocopherols, polyphenols, tocotrienols, BHA, and BHT), chelating agents (e.g., EDTA), and preservatives (e.g., parabens). Examples of suitable antioxidants, preservatives, and chelating agents are listed in pp. 1612–13, 1626, and 1654–55 of the ICI Handbook. In addition, the topical compositions useful herein can contain conventional cosmetic adjuvants, such as dyes, opacifiers (e.g., titanium dioxide), pigments, and fragrances.

The compositions and cosmetic formulations containing such compositions of the present invention may be prepared using methodology that is well known by an artisan of ordinary skill. The following is a description of the manufacturing of cosmetic compositions of the present invention.

EXAMPLE 1

Mineral Water Containing Carnitine, Trehalose, and Sodium Pyruvate (Evian, France)

A composition containing Evian® Mineral Water, carnitine, sodium pyruvate, and trehalose was manufactured using the ingredients listed in Table I.

TABLE I

| INGREDIENTS | % Weight |
| --- | --- |
| L-Carnitine | 1 |
| Sodium Pyruvate | 1 |
| Trehalose | 1 |
| D-Panthenol (75%)/Water (25%) | 1.3 |
| Magnesium Ascorbyl Phosphate | 1 |
| L-Proline | 1 |
| Mineral Water | 72.7 |
| Pentylene Glycol | 20 |
| Phenoxyethanol | 1 |

The mineral water was first heated to 30° C. The other ingredients were then added and dissolved one by one under mixing conditions. The pentylene glycol was obtained from Dragoco Gerberding & Co. (Holzminden, Germany) under the tradename Hydrolite®-5.

EXAMPLE 2

Skin Cleansing Emulsion

A skin cleansing emulsion composition containing the composition of Example 1 was manufactured using the ingredients listed in Table II.

TABLE II

| INGREDIENTS | % WEIGHT |
| --- | --- |
| Oil Phase Ingredients | |
| Isononyl Isononanoate | 2 |
| Cyclomethicone | 2 |
| Isostearyl Palmitate | 2 |
| Cetyl Octanoate | 2 |
| Pentaerythritol Tetraoctanoate | 2 |
| Tocopheryl Acetate | 0.01 |
| Evening Primrose Oil | 0.01 |
| Water Phase Ingredients | |
| Mineral Water | q.s. 100 |
| Carbomer | 0.5 |
| Hexylene Glycol | 1 |
| Sucrose Cocoate | 0.4875 |
| Methyl paraben | 0.4 |
| Propyl paraben | 0.1 |
| Disodium EDTA | 0.1 |
| Neutralization Ingredient | |
| 20% Sodium Hydroxide | 0.1360 |
| Post Addition Ingredient | |
| Arnica Montana Extract 5–10%/Propylene Glycol 40–70%/water 25–50% | 0.1 |
| Sodium Pyruvate | 0.04 |
| Peg-6 Caprylic-capric Glycerides | 0.75 |
| Composition of Example 1 | 1 |
| Fragrance | 0.05 |

The mineral water (Evian® Mineral Water from Evian, France) and the disodium EDTA were heated to 85° C., and heat was maintained for about 15 min. The carbomer (Carbopol Ultrez® 10 from BF Goodrich Performance Materials, Consumer Specialties Group, Cleveland Ohio) was slowly added to the mixture and mixed for about 20 min. The mixture was then cooled to 65° C., following which the Peg-6 caprylic-capric glycerides (Tegosoft® GMC6 from Tegasoft Co., Th Goldschmit AG, Essen, Germany), sucrose cocoate, hexylene glycol, methyl paraben, and propyl paraben were added. In a separate beaker, the Oil Phase Ingredients were mixed and heated to 60° C. (with the tocopheryl acetate and evening primrose oil being added just before mixing with the mixture in the first beaker). The mixture of the second beaker was added to the water phase and mixed for about 15 min. The mixture was then neutralized with the 20% sodium hydroxide aqueous solution and mixed until uniform. The mixture was then cooled to 35° C., and the sodium pyruvate, carnitine, Arnica Montana Extract/Propylene Glycol/Water (Vegetol Arnica MCF 115 Hydro® from Gattefosse SA, Saint Priest Cedex, France), and the composition of Example 1 were added. Finally, the fragrance was then added to the resulting mixture.

EXAMPLE 3

Body Mist

A body mist composition containing the composition of Example 1 is manufactured using the ingredients listed in Table III.

TABLE III

| INGREDIENTS | % Weight |
| --- | --- |
| Water Phase Ingredients | |
| Mineral Water | q.s. 100 |
| Disodium EDTA | 0.01–1 |
| Carbomer | 0.1–1 |
| Sorbitol (70%)/water (30%) | 1–10 |
| Butylene glycol | 1–10 |
| PEG-20 methyl glucose sesquistearate | 1–10 |
| Glycereth-26 | 0.1–1 |
| Propyl paraben | 0.001–1 |
| Phenoxyethanol | 0.1–5 |
| Methyl paraben | 0.1–1 |
| Oil Phase Ingredients | |
| Octyl palmitate | 0.1–10 |
| Methyl glucose sesquistearate | 0.1–1 |
| Cetyl alcohol | 0.1–1 |
| Glyceryl stearate 50%/PEG-100 stearate 50% | 0.1–1 |
| Isohexadecane | 1–10 |
| Cyclomethicone | 0.1–1 |
| Tromethamine Mixture | |
| Mineral Water | 1–10 |
| Tromethamine | 0.1–1 |
| Trehalose Mixture | |
| Mineral Water | 1–10 |
| Trehalose | 0.01–0.1 |
| Post Addition Ingredients | |
| Composition of Example 1 | 0.1–1 |
| Evening primrose oil | 0.001–.01 |
| Vitamin E acetate | 0.001–0.1 |
| Fragrance | 0.1–1 |

First, the PEG-20 methyl glucose sesquistearate is preheated to 50° C. The water phase is formed by first mixing the mineral water and the disodium EDTA of the Water Phase Ingredients, and then heating the resulting mixture to 85° C. for 15 minutes. Next, the mixture is cooled to 80° C., and the carbomer is added and mixed for 40 minutes, resulting in the formation of a gel. Next, the butylene glycol and the sorbitol mixture are added to the mixture and mixed until homogenous. Then, the PEG-20 methyl glucose sesquistearate and the glycereth-26 are added to the mixture, and mixed until homogenous. Finally, the remaining Water Phase Ingredients are added to the mixture.

To form the oil phase, all of the Oil Phase Ingredients, other than the cyclomethicone, are heated to 80° C. and mixed until homogenous. Ten minutes prior to adding the oil phase into the water phase, the cyclomethicone is added and mixed with the oil phase mixture. Following the addition and mixture of the oil phase into the water phase, the resulting emulsion is cooled to 75° C. Then, the Tromethamine Mixture is added to the emulsion, and homogenized for 20 minutes. The resulting emulsion is then cooled to 35° C., at which time the Trehalose Mixture is added. Once the emulsion had further cooled to 30° C., the Post Addition Ingredients are added and mixed into the emulsion.

EXAMPLE 4

Moisturizing Skin-Care Composition (MOON)

A moisturizing skin-care composition containing the composition of Example 1 is manufactured using the ingredients listed in Table IV.

TABLE IV

| INGREDIENTS | % WEIGHT |
|---|---|
| Water Phase Ingredients | |
| Mineral Water | q.s. 100 |
| Panthenol 75%/water 25% | 0.01–0.1 |
| Disodium EDTA | 0.1–1 |
| Methyl paraben | 0.1–1 |
| Propyl paraben | 0.01–1 |
| Glycerin | 1–10 |
| Pentylene Glycol | 1–10 |
| Trehalose | 0.1–1 |
| Xanthan Gum | 0.1–1 |
| Magnesium Ascorbyl Phosphate | 0.001–0.1 |
| Water/Propylene Glycol/Honeysuckle Extract | 0.01–0.1 |
| Propylene Glycol/Water/Pansy Extract | 0.01–0.1 |
| Composition of Example 1 | 0.1–10 |
| Carbomer | 0.1–1 |
| 20% Sodium Hydroxide in water | 0.1–1 |
| Oil Phase Ingredients | |
| Water 50%/caprylic-capric triglyceride 5–10%/pentylene glycol 5%/hydrogenated lecithin 6%/glycerin 3%/butyrospermum parkii 1–5%/squalane 1–5%/ceramide 0.1% | 1–10 |
| Cyclomethicone and Dimethicone Crosspolymer | 1–10 |
| Macadamia Nut Oil | 1–10 |
| Caprylic-Capric Triglyceride | 1–10 |
| Avocado Oil | 0.1–5 |
| Hexyldecyl Stearate | 1–20 |
| Cetyl Alcohol | 0.1–1 |
| Tocopheryl Acetate | 0.05–0.5 |
| Retinyl Palmitate | 0.01–0.1 |
| Evening Primrose Oil | 0.01–0.1 |
| Post Addition Ingredient | |
| Fragrance | 0.01–1 |

The glycerin, honey suckle extract, pansy extract, panthenol mixture, trehalose, Composition of Example 1, and Magnesium ascorbyl phosphate are mixed in a first beaker. The pentylene glycol, methyl paraben, and propyl paraben are mixed in a second beaker. The hexyldecyl stearate and cetyl alcohol are mixed in a third beaker.

In a fourth beaker, the mineral water and disodium EDTA are heated to 85° C. and maintained for about 15 min. The water is then cooled to 70° C., and the xanthan gum is slowly added and mixed until uniform. Once the mixture has cooled to 65° C., the carbomer is added and mixed until completely dispersed. Once cooled to about 42° C., the mixture is neutralized with the sodium hydroxide solution. Once cooled to about 30° C., the mixture of the first beaker is added to the fourth beaker and mixed until uniform, following which the mixture in the second beaker is added to the fourth beaker.

In a fifth beaker, the remaining Oil Phase Ingredients are combined and mixed until uniform. The mixture in the third baker is then heated to 60° C. and added to the oil phase in the fifth beaker. The resulting oil phase in the fifth beaker is then added to the aqueous phase in the fourth beaker under mixing conditions. Once the mixtures have cooled to 35° C., the fragrance is added to the resulting emulsion.

EXAMPLE 5

Cleansing Gel

A cleansing gel containing the composition of Example 1 was manufactured using the ingredients listed in Table V.

TABLE V

| INGREDIENTS | % WEIGHT |
|---|---|
| Premix Addition Ingredients | |
| Tocopheryl Acetate | 0.001–0.1 |
| Evening Prim Rose Oil | 0.001–0.1 |
| Polysorbate 20 | 1–10 |
| Fragrance Addition Ingredients | |
| Fragrance | 0.1–1 |
| Polysorbate 20 | 0.1–1 |
| Cocamidopropyl Betaine | 0.1–1 |
| Water Addition Ingredients | |
| Mineral Water | q.s. 100 |
| Sodium Laureth (2) Sulfate 70%/Water 30% | 1–10 |
| Cocamidopropyl Betaine | 1–10 |
| Disodium Lauroamphodiacetate | 1–10 |
| PEG 150 Distearate | 1–10 |
| Phenoxyethanol | 0.5–5 |
| Disodium EDTA | 0.1–1 |
| Iodopropynyl butyl carbamate 10%/PEG-4 laurate 90% | 0.01–1 |
| 10% Citric Acid | 0.5–5 |
| Colorant | 0.0001–0.001 |
| Post Addition Ingredients | |
| Sodium Pyruvate | 0.01–0.1 |
| Carnitine | 0.01–0.1 |
| Composition of Example 1 | 0.1–10 |
| Arnica Montana extracts 5–10%/Water 25–50%/Propylene Glycol 40–70% | 0.01–1 |

In a first beaker, the Premix Addition Ingredients are mixed together and heated to 50° C. In a second beaker, the Fragrance Addition Ingredient's polysorbate 20 and cocamidopropyl betaine are mixed together and heated to 40° C. The fragrance is then added to a second beaker, and the resulting ingredients are mixed until clear and uniform.

In a third beaker, the mineral water and disodium EDTA is heated to 85° C., and the heat is maintained for about 15 min. The sodium laureth(2) sulfate, cocamidoproylpropyl betaine, and disodium lauroamphodiacetate are then added to the third beaker and mixed, followed by the addition of PEG-150 distearate. The resulting mixture is then homogenized. The Iodopropynyl butyl carbamate/PEG-4 laurate, premixed with phenoxyethanol, is then added to the third baker and mixed. The contents of the first beaker are then added to the second beaker, following which the resulting mixture was cooled to 60° C. The colorant is then added and mixed until clear and homogeneous. The citric acid solution is then added to the third beaker. When the mixture had cooled to 35° C., the post addition ingredients and the mixture in the second baker are added to the third beaker and mixed until uniform.

EXAMPLE 6

Sunscreen Moisturizer

A sunscreen moisturizing composition containing the composition of Example 1 and the sunscreen octyl methoxycinnamate is manufactured using the ingredients listed in Table VI.

TABLE VI

| INGREDIENTS | % Weight |
|---|---|
| Water Phase Ingredients | |
| Mineral Water | q.s. 100 |
| Disodium EDTA | 0.1 |
| Glycerin | 3 |
| Butylene glycol | 3 |
| Carbomer | 0.25 |
| Acrylate-C10-30 alkyl acrylate crosspolymer | 0.07 |
| Glyceryl polymethacrylate 67%/water 32%/propylene glycol 1% | 5 |
| Propyl paraben | 0.201 |
| Methyl paraben | 0.35 |
| Phenoxyethanol | 0.584 |
| Oil Phase Ingredients | |
| Cetearyl alcohol | 1 |
| C12–C15 alkyl benzoate | 4 |
| Potassium cetyl phosphate | 1.5 |
| PEG-100 stearate 50%/glyceryl stearate 50% | 0.3 |
| Di-C12–13 alkyl malate | 5 |
| Talc | 1 |
| Phenoxyethanol | 0.365 |
| Propyl paraben | |
| Methyl paraben | |
| Iodopropynyl butylcarbamate 10%/PEG-4 laurate 90% | 0.1 |
| Octyl methoxycinnamate | 7.5 |
| Butyl methoxydibenzoylmethane | 3 |
| Tocopheryl acetate | 1 |
| Tromethamine Mixture | |
| Mineral Water | 2 |
| Tromethamine | 0.3 |
| Trehalose Mixture | |
| Mineral Water | 2 |
| Trehalose | 0.25 |
| Post Addition Ingredients | |
| Cyclomethicone | 2 |
| Composition of Example 1 | 1 |
| Evening primrose oil | 0.01 |
| Fragrance | 0.3 |

To form the water phase, the mineral water (Evian® Mineral Water, Evian, France) of the Water Phase Ingredients was heated to 85° C. and stirred for about 15 minutes in a first beaker. The disodium EDTA, glycerin, and butylene glycol were then added to the first beaker and stirred for an additional 10 minutes. The first beaker was then cooled to 82° C. Next, the carbomer and the acylate-C10-30 alkyl acrylate crosspolymer were dispersed in the mixture in the first beaker and stirred for about 25 minutes until the mixture gelified. The remaining Water Phase Ingredients were then added to the first beaker and mixed.

To form the oil phase, the Oil Phase Ingredients were added to a second beaker, heated to 85° C., and mixed for 15 minutes. The oil phase mixture in the second beaker was then added to the first beaker under mixing conditions to form an emulsion. The emulsion was then cooled to 25° C.

and neutralized with the Tromethamine Mixture. Next, the cyclomethicone was mixed into the emulsion for 15 minutes. Lastly, the Trehalose Mixture, the composition of Example 1, the evening primrose oil, and the fragrance were added to the resulting mixture and mixed until uniform.

EXAMPLE 7

Lip Balm

An oil-in-water emulsion cosmetic lip balm containing the composition of Example 1 is manufactured using the following ingredients listed in Table VII.

TABLE VII

| INGREDIENTS | % Weight |
|---|---|
| Oil Phase Ingredients | |
| Cetyl Alcohol | 1–10 |
| Hexyldecyl Stearate | 10–50 |
| Trimethylated Silica 50%/Decamethyl Cyclopentasiloxane 50% | 1–10 |
| Macadamia Nut Oil | 0.1–10 |
| Avocado Oil | 0.1–10 |
| Tocopheryl Acetate | 0.01–1 |
| Vitamin A Palmitate | 0.01–0.1 |
| Evening Primrose Oil | 0.01–0.1 |
| Cyclomethicone and Dimethicone Crosspolymer | 1–10 |
| Water Phase Ingredients | |
| Mineral Water | q.s. 100 |
| Hydroxyethylcellulose | 0.1–1 |
| Methylparaben | 0.1–1 |
| Propyl paraben | 0.01–0.1 |
| Phenoxyethanol | 0.1–1 |
| Panthanol | 0.1–1 |
| Glycerin | 1–10 |
| Disodium EDTA | 0.05–0.5 |
| Proline | 0.01–0.1 |
| Potassium Cetyl Phosphate | 1–10 |
| Post Addition Ingredients | |
| Trehalose | 0.1–1 |
| Flavor/Fragrance | 0.001–5 |
| Magnesium Ascorbyl Phosphate | 0.05–0.5 |
| Composition of Example 1 | 0.1–10 |

The Oil Phase Ingredients are added to a first beaker and heated to 80–85° C. The mineral water is then added to a second beaker, and the mineral water is heated and stirred. The hydroxyethylcellulose is then sprinkled into the heated water. The water then continues to mix at a low speed until a uniform gel is observed. The water temperature is maintained at 80–85° C., and the remaining Water Phase Ingredients are added, with the potassium cetyl phosphate being added last. Upon the addition of the potassium cetyl phosphate, a minimum mixing speed is used to avoid aeration.

With both phases heated to about 85° C., the oil phase is poured into water phase. The mixing speed is increased as needed while avoiding aeration, and the resulting emulsion is allowed to cool during phase homogenization for about 15 minutes. At or below 40° C., the Post Addition Ingredients are added followed by a second homogenization for 10 minutes. The resulting mixture is then allowed to cool to room temperature.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A cosmetic composition comprising (i) carnitine or a cosmetically acceptable salt or ester thereof, (ii) pyruvic acid or a cosmetically acceptable salt or ester thereof, (iii) a nutrient selected from the group consisting of vitamins or a cosmetically acceptable salt or ester there of, essential amino acids or a cosmetically acceptable salt or ester thereof, and essential fatty acids, and (iv) trehalose or a cosmetically acceptable salt or ester thereof.

2. A composition of claim 1, wherein said nutrient is selected from the group consisting of vitamin A, vitamin C, vitamin E, an essential amino acid and a cosmetically acceptable salt or ester thereof.

3. A composition of claim 1, wherein said composition further comprises mineral water.

4. A composition of claim 2, wherein said composition further comprises mineral water.

5. A topical cosmetic composition comprising (i) carnitine or a cosmetically acceptable salt or ester thereof, (ii) pyruvic acid or a cosmetically acceptable salt or ester thereof, (iii) a nutrient selected from the group consisting of vitamins or a cosmetically acceptable salt or ester thereof, essential amino acids or a cosmetically acceptable salt or ester thereof, and essential fatty acids, and (iv) trehalose or a cosmetically acceptable salt or ester thereof and (v) a cosmetically-acceptable topical carrier.

6. A composition of claim 5, wherein said nutrient is selected from the group consisting of vitamin A, vitamin E, an essential amino acid, and a cosmetically acceptable salt or ester thereof.

7. A composition of claim 5, wherein said composition further comprises mineral water.

8. A composition of claim 6, wherein said composition further comprises mineral water.

9. A composition of claim 1, wherein said pyruvic or a cosmetically acceptable salt or ester thereof is sodium pyruvate.

10. A composition of claim 1, wherein said carnitine or a cosmetically acceptable salt or ester thereof is L-carnitine.

11. A composition of claim 9, wherein said carnitine or a cosmetically acceptable salt or ester thereof is L-carnitine.

12. A composition of claim 11, wherein said trehalose or a cosmetically acceptable salt or ester thereof is trehalose.

13. A composition of claim 5, wherein said pyruvic acid or a cosmetically acceptable salt or ester thereof is sodium pyruvate.

14. A composition of claim 5, wherein said carnitine or a cosmetically acceptable salt or ester thereof is L-carnitine.

15. A composition of claim 13, wherein said carnitine or a cosmetically acceptable salt or ester thereof is L-carnitine.

16. A composition of claim 15, wherein said trehalose or a cosmetically acceptable salt or ester thereof is trehalose.

17. A composition of claim 9, wherein said composition further comprises mineral water.

18. A composition of claim 10, wherein said composition further comprises mineral water.

19. A composition of claim 11, wherein said composition further comprises mineral water.

20. A composition of claim 12, wherein said composition further comprises mineral water.

21. A composition of claim 13, wherein said composition further comprises mineral water.

22. A composition of claim 14, wherein said composition further comprises mineral water.

23. A composition of claim 15, wherein said composition further comprises mineral water.

24. A composition of claim 16, wherein said composition further comprises mineral water.

* * * * *